(12) United States Patent
Yasumura et al.

(10) Patent No.: US 8,232,429 B2
(45) Date of Patent: Jul. 31, 2012

(54) METHODS FOR PRODUCING OXIDIZED CYCLIC PHENOL SULFIDES

(75) Inventors: Masateru Yasumura, Ibaraki (JP); Yoshikazu Aoki, Fukushima (JP); Masami Ito, Ibaraki (JP); Masafumi Umekawa, Fukushima (JP); Naohiro Tarumoto, Tokyo (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 271 days.

(21) Appl. No.: 12/503,895

(22) Filed: Jul. 16, 2009

(65) Prior Publication Data

US 2009/0275783 A1 Nov. 5, 2009

Related U.S. Application Data

(63) Continuation of application No. PCT/JP2008/050420, filed on Jan. 16, 2008.

(30) Foreign Application Priority Data

Jan. 16, 2007 (JP) ................................. 2007-006485

(51) Int. Cl.
*C07C 315/00* (2006.01)
(52) U.S. Cl. ........................................... 568/27; 568/54
(58) Field of Classification Search .................. None
See application file for complete search history.

(56) References Cited

U.S. PATENT DOCUMENTS 5,998,631 A * 12/1999 Kumagai et al. ................ 549/11

FOREIGN PATENT DOCUMENTS

| EP | 0882724 A1 | 12/1992 |
| JP | 226882 | 11/1989 |
| WO | 9809959 | 12/1998 |

OTHER PUBLICATIONS

International Search Report for PCT Application No. PCT/JP2008/050420.
Written Opinion of the International Searching Authority for PCT/JP2008/050420.
Morohashi, et al. Selective oxidation of thiacalix[4]arenes to the sulfinyl and sulfonyl counterparts and their complexation abilities toward metal ions as studied by solvent extraction, Tetrahedron 57 (2001) 5557-5563.
Lhotak, et al. Stereoselective oxidation of thiacalix[4]arenes with the NaNO3/CF3COOH system, Tetrahedron Letters 44 (2003) 7333-7336.
Mislin, et al. Tetrasulfinylcalix[4]arenes : Synthesis and Solid State Structural Analysis; Tetrahedron Letters 40 (1999) 1129-1132.
Iki, et al. Selective Oxidation of Thiacalix[4]arenes to the Sulfinyl- and Sulfonylcalix[4]arenes and Their Coordination Ability to Metal Ions, Tetrahedron Letters 39 (1998) 7559-7562.
Mislin, et al., Sulfone-calixarenes: a new class of molecular building block, Chem. Commun., 1998, 1345-134.
Morohashi, et al. Thiacalixarene: A New Molecular Scaffold for Host Molecules, Journal of Synthetic Organic Chemistry (Japan), vol. 60, No. 6, Jun. 2002, 550-562.

* cited by examiner

*Primary Examiner* — Sudhakar Katakam
(74) *Attorney, Agent, or Firm* — Hoffmann & Baron, LLP

(57) ABSTRACT

A method for producing an oxidized cyclic phenol sulfide which comprises the step of oxidizing a cyclic phenol sulfide of the following formula (1) as a raw material:

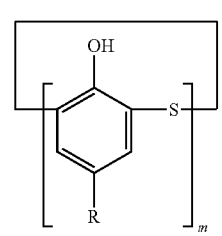

(1)

wherein R represents a straight or branched alkyl group having 1 to 6 carbon atoms, and m is an integer from 4 to 8, in a solvent(s) other than a halogenated hydrocarbon in an amount of 2 or more and less than 10 parts by weight per 1 part by weight of the cyclic phenol sulfide, with an oxidizing agent(s) to obtain an oxidized cyclic phenol sulfide of the following formula (2):

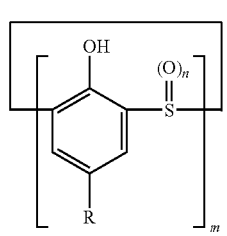

(2)

wherein R represents a straight or branched alkyl group having 1 to 6 carbon atoms, m is an integer from 4 to 8, and n is 1 or 2.

12 Claims, 6 Drawing Sheets

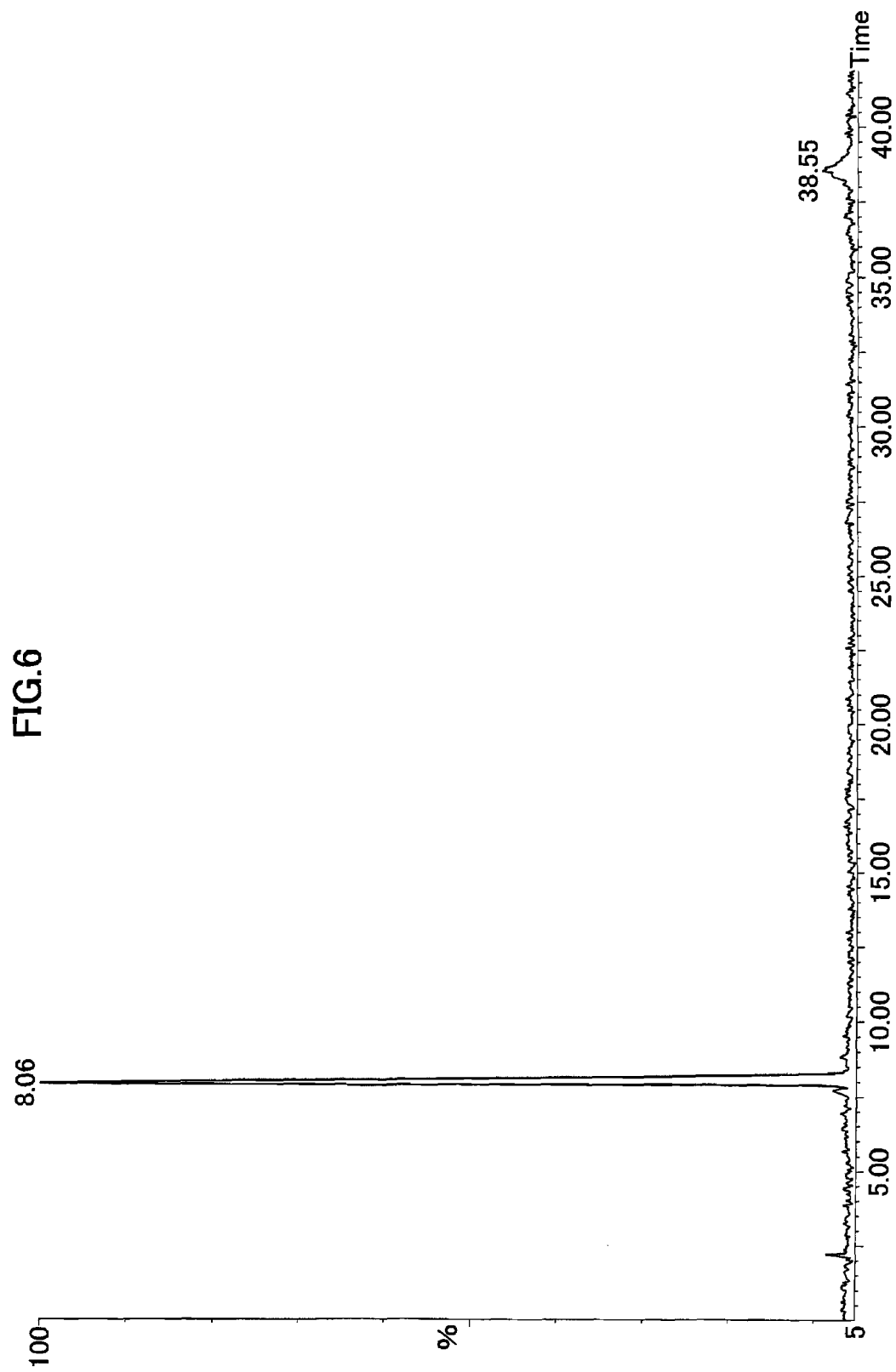

METHODS FOR PRODUCING OXIDIZED CYCLIC PHENOL SULFIDES

CROSS-REFERENCE TO RELATED APPLICATIONS

This application is a Continuation of International Application No. PCT/JP2008/050420, filed Jan. 16, 2008, which claims the benefit of Japanese Application No. 2007-006485, filed Jan. 16, 2007, the contents of all of which are incorporated by reference herein in their entirety.

FIELD OF THE INVENTION

The present invention relates to methods for producing oxidized cyclic phenol sulfides, which are useful as metal capture agents or solidifying agents wherein the metal-ion capturing ability thereof is used; optical sensors, ion sensors or substrate specific sensors wherein the recognizing ability of ions or molecules is used; materials for separation membranes and intermediates thereof, charge control agents; catalysts, and the like.

BACKGROUND OF THE INVENTION

Until now, as the method for producing an oxidized cyclic phenol sulfide, it is known that there is the method which comprises the step of oxidizing a corresponding cyclic phenol sulfide. Examples of oxidizing agents used for oxidation reaction include hydrogen peroxide, organic peroxides, peracids, halogen oxides, N-halogen compounds, halogen molecules, oxygen, ozone, a nitric acid, and inorganic oxides. Hydrogen peroxide, halogen molecules, and inorganic oxides such as sodium perborate are preferable among them. Though a preferable solvent varies depending on the kind of an oxidizing agent, it is proposed to use halogenated hydrocarbon solvents such as chloroform and dichloromethane; alcohols such as methanol and ethanol; acetonitrile; polar solvents such as an acetic acid and water, and the like. Further, it is also known that, if necessary, catalysts such as vanadium (V) oxide, sodium metavanadate (V), titanium trichloride, tungsten (VI) oxide and sodium phosphate can be used in oxidation reaction.

Thus, various combinations of an oxidizing agent/a solvent/a catalyst are proposed to be used in oxidation of sulfide bond of a cyclic phenol sulfide of formula (A) (refer to Patent Literature 1, for example):

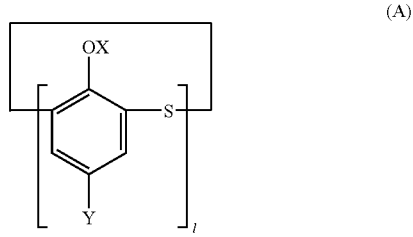

(A)

wherein X represents a hydrogen atom, a hydrocarbon group, or an acyl group; Y represents a hydrogen atom, a hydrocarbon group, a halogenated hydrocarbon group, —COR1, —OR2, —COOR3, —CN, —CONH$_2$, —NO$_2$, —NR4R5, a halogen atom, —SO$_4$R6, or —SO$_3$R7, in which R1, R2, R3, R4, R5, R6, and R7 each represents a hydrogen atom or a hydrocarbon group; and l represents an integer of 4 to 12.

However, the literature discloses that 10 to 50 mL of a solvent is preferably used per 1 g of a cyclic phenol sulfide, which is rather a large quantity of a solvent; that the reaction temperature is preferably 15 to 65° C. when using an inorganic oxide, which is rather a mild range of the embodiment; and that the reaction is conducted for over 2 days until oxidation to a sulfonyl group is completed, which is a long period of time. Further, it discloses that phenolate substituent X is a hydrogen atom, a hydrocarbon group or an acyl group. However, since a compound wherein X is a hydrogen atom is applied to a metal capture agent, purity of an oxidized compound wherein X is a hydrogen atom is not paid attention to. Practically, widely used is the method which comprises the step of oxidizing a cyclic phenol sulfide with sodium perborate or hydrogen peroxide in a halogenated hydrocarbon solvent(s) such as chloroform and in the presence of an acetic acid (refer to Non-patent Literatures 1 to 3, for example).

The reason why a halogenated hydrocarbon solvent is widely used is that though the cyclic phenol sulfide of the formula (A) is poorly soluble in most solvents, it is relatively well soluble in a halogenated hydrocarbon solvent such as chloroform as compared to other solvents. In addition to it, when using ketone, ester, or ether solvents as well as proposed alcohol solvents in the presence of an oxidizing agent, there are risks such as explosion and fire derived from the peroxide production of a solvent itself. This is also the reason why a halogenated hydrocarbon solvent such as chloroform is widely used. Thus, though a halogenated hydrocarbon solvent is practically widely used in oxidation of the cyclic phenol sulfide of the formula (A), usage thereof seriously damages the environment as is well known. Therefore, it would be difficult from both the cost and environmental aspects that a halogenated hydrocarbon solvent is applied on industrial scale where the usage amount thereof becomes large.

Meanwhile, an oxidized cyclic phenol sulfide obtained by oxidizing the cyclic phenol sulfide of the formula (A) is actively studied as a substance which has a variety of possible industrial applicability such as a third-generation inclusion molecule and a static charge control agent which is studied by the present inventors.

However, it is still impossible to develop the environmentally conscious and highly productive production method thereof which is applicable on industrial scale, and the compound is hardly industrially applicable. In order to promote wide use of such a useful substance on the industrial field, it has been eagerly desired to develop the production method thereof which is industrially applicable.

Patent Literature 1: WO98/09959
Non-patent Literature 1: TETRAHEDRON LETTERS 39 (1998) 7559-7562
Non-patent Literature 2: TETRAHEDRON 57 (2001) 5557-5563
Non-patent Literature 3: J. CHEM. SOC., CHEM. COMMUN., 1998, 1345

SUMMARY OF THE INVENTION

The object of the present invention is to provide environmentally-friendly, highly productive and industrially applicable production methods which comprise the step of oxidizing a cyclic phenol sulfide of following formula (1) to obtain an oxidized cyclic phenol sulfide of following formula (2).

The inventors have thoroughly searched to solve the above problems and completed the present invention based on the following finding. Namely, the present invention provides a method for producing an oxidized cyclic phenol sulfide which comprises the step of oxidizing a cyclic phenol sulfide of the following formula (1) as a raw material:

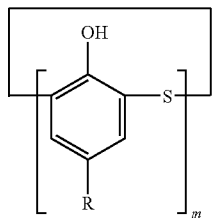
(1)

wherein R represents a straight or branched alkyl group having 1 to 6 carbon atoms, and m is an integer from 4 to 8, in a solvent(s) other than a halogenated hydrocarbon in an amount of 2 or more and less than 10 parts by weight per 1 part by weight of the cyclic phenol sulfide, with an oxidizing agent(s) to obtain an oxidized cyclic phenol sulfide of the following formula (2):

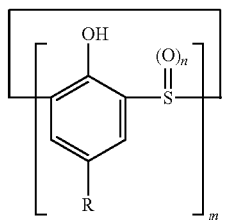
(2)

wherein R represents a straight or branched alkyl group having 1 to 6 carbon atoms, m is an integer from 4 to 8, and n is 1 or 2.

According to the method for producing an oxidized cyclic phenol sulfide of the present invention, since oxidation smoothly proceeds even in the state where the starting material of the formula (1) is dispersed in a solvent(s), there are advantages that solvent usage can be drastically decreased and the reaction time can be shortened. Therefore, it is possible to easily produce the oxidized cyclic phenol sulfide of the formula (2) in high yields, wherein a content of impurities is low, together with improving productive efficiency and decreasing costs as compared to prior arts. As a result, it is possible to easily filter and separate the reaction mixture without conducting a complicated treatment step to obtain the oxidized cyclic phenol sulfide of the formula (2).

Further, since no halogenated hydrocarbon solvent is used, it is possible to produce the oxidized cyclic phenol sulfide of the formula (2) with reducing environmental burdens.

BRIEF DESCRIPTION OF THE DRAWINGS

FIG. 6 shows an LC/MS (TIC) chart of the oxidized cyclic phenol sulfide obtained by Example 3.

DETAILED DESCRIPTION OF THE INVENTION

Figure 1:
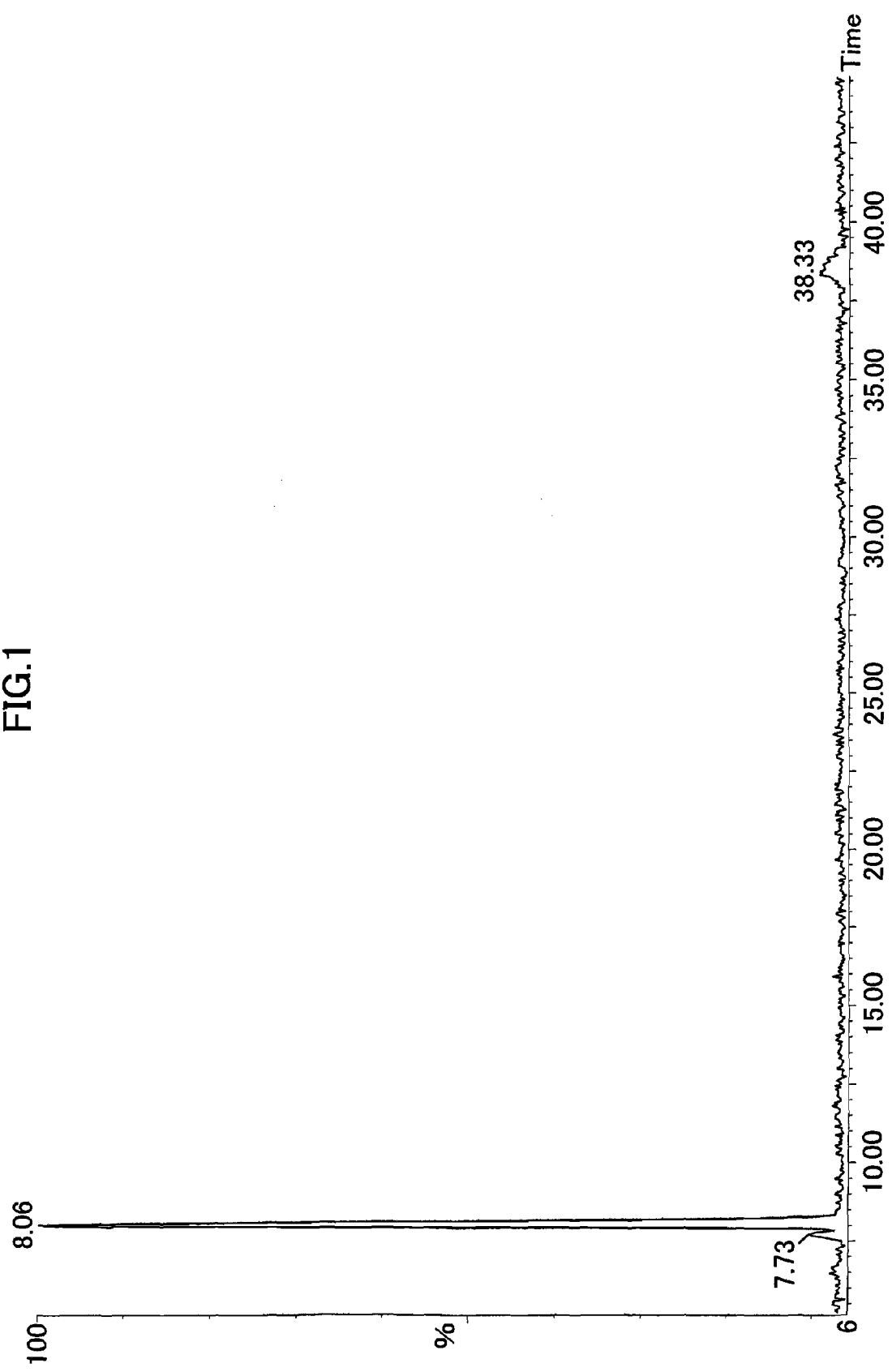
FIG. 1 shows an LC/MS (TIC) chart of the oxidized cyclic phenol sulfide obtained by Example 1.

In a cyclic phenol sulfide which is used as a raw material of the present invention, examples of a straight or branched alkyl group having 1 to 6 carbon atoms represented by R in the formula (1) include following groups: a methyl group, ethyl group, n-propyl group, 2-propyl group, n-butyl group, sec-butyl group, 2-methylpropyl group, tert-butyl group, n-pentyl group, 1-methylbutyl group, 1-ethylpropyl group, 1,1-dimethylpropyl group, 1,2-dimethylpropyl group, n-hexyl group, 1-methylpentyl group, 2-methylpentyl group, 3-methylpentyl group, 4-methylpentyl group, 1-ethylbutyl group, 2-ethylbutyl group, 1,1-dimethylbutyl group, 1,2-dimethylbutyl group, 1,3-dimethylbutyl group, 1,4-dimethylbutyl group, 2,2-dimethylbutyl group, 2,3-dimethylbutyl group, 3,3-dimethylbutyl group, 1-ethyl-2-methyl-propyl group, and 1,1,2-trimethylpropyl group. Further, the cyclic phenol sulfide which is a raw material of the present invention can be filtered after the synthetic reaction thereof, and thus obtained crystals can be used as a raw material of oxidation reaction without a step of purifying said crystals.

In an oxidized phenol sulfide of the formula (2) of the present invention, n is 1 or 2, and n of each molecules may be the same or different from each other, and it is preferable that each molecule satisfies $1.5\ m \leq N \leq 2\ m$ when defining a total of n as N. Further preferable range of N is $1.7\ m \leq N \leq 2\ m$.

Next, the method for producing an oxidized cyclic phenol sulfide of the present invention is illustrated. In the present invention, it is preferable that an organic carboxylic acid not comprising a halogen atom is used as a solvent used in the oxidation reaction. Examples thereof include an acetic acid, a propionic acid and a butyric acid, and an acetic acid is particularly preferable. According to the production method of the present invention, there is an advantage that oxidation proceeds even in the state where the cyclic phenol sulfide of the formula (1), which is a raw materials, is dispersed in a solvent(s). Thus, there is no need to use an extra amount of a solvent for preparing a solution state, and the reaction can be conducted in 2 or more and less than 10 parts by weight of an organic carboxylic acid per 1 part by weight of the cyclic phenol sulfide of the formula (1). 2 to 7 parts by weight thereof is preferable, and 3 to 5 parts by weight thereof is more preferable.

In the present invention, various oxidizing agents can be used as the oxidizing agent used in the oxidation reaction, e.g., hydrogen peroxide, sodium perborate, sodium perchlorate, and an m-chloroperbenzoic acid. Hydrogen peroxide water is preferable among them, and 35% hydrogen peroxide water is more preferable from the viewpoint of safe handling.

Usage of hydrogen peroxide is preferably 4 to 24 in mole ratios per 1 mole of the cyclic phenol sulfide of the formula (1) and particularly preferably 8 to 16 in mole ratios.

In the present invention, the reaction can be promoted by making a metal catalyst(s) coexist in the oxidation reaction. It is possible to use various metal catalysts such as vanadium (V) oxide, sodium metavanadate (V), tungsten (VI) oxide and sodium phosphate and cobalt acetate. A tungsten acid and sodium tungstate are preferable, and sodium tungstate is particularly preferable. The usage thereof is preferably 0.01 to 40 mol % per 1 mole of the cyclic phenol sulfide of the formula (1), and particularly preferably 10 to 20 mol %.

The reaction rate can be increased without affecting the reaction composition by adding metal carboxylate in advance or during the reaction in addition to a metal catalyst(s). A preferable example of metal carboxylate which is a reaction accelerator is metal acetate, and sodium acetate is particularly preferable. The usage thereof is preferably 0.01 to 5 in mole ratios per 1 mole of a metal catalyst and more preferably 1 to 2.5 in mole ratios.

In the present invention, when using hydrogen peroxide as an oxidizing agent, it is preferable that hydrogen peroxide water is added dropwise under heating to a mixture comprising the cyclic phenol sulfide of the formula (1), a solvent, a catalyst and a reaction accelerator. Though it is possible to previously pour a total amount of hydrogen peroxide water together with the mixture and proceed with the reaction, it is particularly preferable to add it dropwise for safety. In the present invention, the start temperature of hydrogen peroxide oxidation is about 60° C. When the temperature is lower than 60° C., hydrogen peroxide accumulates and it carries runaway risk when heating. Therefore, in order to start oxidation safely and smoothly, it is preferable that the reaction mixture is previously heated up to 60° C. and then hydrogen peroxide water is added dropwise thereto. Though this oxidation reaction is exothermic reaction and heat evolution is especially seen at the beginning of the reaction, the method of the present invention has an advantage of controlling heat evolution by controlling the drop rate of hydrogen peroxide. Basically, when and after adding dropwise hydrogen peroxide water in an amount of 8 molar equivalent per 1 mole of the cyclic phenol sulfide of the formula (1), heat evolution is hardly seen. Though the drop time is not particularly limited, it is preferably 1 to 3 hours. After the drop of an oxidizing agent (hydrogen peroxide water) is completed, the temperature may be maintained until the end of the reaction, or it is possible to speed up the reaction procedure by gradually heating. Though the heating temperature and the reaction time in said temperature are not particularly limited, it is preferable to conduct the reaction for 15 to 18 hours at 60° C., then for 2 to 3 hours after heating it up to 70° C., and then for 2 to 5 hours (more preferably 2 to 3.5 hours) after heating it up to 80° C. or higher (more preferably 80° C.).

The oxidation reaction mixture, which exists in a solvent in dispersion state, is cooled down to appropriate temperature after the completion of the reaction, and, without any complicated treatment step, it is just filtered and washed to easily separate and obtain only a reaction product. Though the cooling temperature is not particularly limited, it is preferable to cool down the mixture to room temperature.

When using the reaction product of the present invention as a static charge control agent, it is preferable to add a mineral acid in mole ratios of 0.01 to 10, and more preferably 2 to 4 per 1 mole of the cyclic phenol sulfide of the formula (1) at the end of the oxidation reaction. Though the temperature and time when adding a mineral acid are not particularly limited, it is preferable to add a mineral acid for 1 hour at 80° C. which is the same temperature as the final temperature in the oxidation reaction. Since a part of the oxidized cyclic phenol sulfide of the formula (2) which is the reaction product remains as metal phenolate, the object of this treatment with a mineral acid is to hydrolyze metal phenolate and decrease a content of metal salts of impurities in the oxidation product. In the case of not treating with a mineral acid, metal residual volume in the oxidized cyclic phenol sulfide of the formula (2) is beyond 1000 ppm and, therefore, decreased charging performance is seen. On the other hand, in the case of treating with a mineral acid, metal residual volume is limited to 1000 ppm or lower and, therefore, it is possible to obtain an oxidized cyclic phenol sulfide of which charging performance is not decreased. Examples of used mineral acids include a hydrochloric acid, a sulfuric acid, a nitric acid, a phosphoric acid, and a boric acid. Though a used mineral acid is not particularly limited, a hydrochloric acid is preferable since inorganic salts which are produced by hydrolysis are easily removed when filtering and washing.

Next, Examples will further illustrate the present invention. They only explain the present invention and do not particularly limit the invention.

EXAMPLE 1

The purity and relative proportions of an oxidized cyclic phenol sulfide produced by the method of the present invention were analyzed by a high-performance liquid chromatography (herein after referred to as HPLC), and the structure thereof was analyzed by LC/MS measurement. The measurement condition of HPLC is as follows: device: LC-10A by Shimadzu Corporation; column: Develosil ODS-HG-5 (inside diameter 4.6 mm, column length 250 mm) by Nomura Chemical Co., Ltd.; column temperature: 40° C.; mobile phase: tetrahydrofuran/acetonitrile/water/trifluoroacetic acid=350/350/300/2 (v/v/v/v); current speed: 1.0 mL/min.; filling amount: 1 μL; and concentration of a sample: 1000 ppm. The measurement condition of LC/MS is as follows: (1) HPLC measurement condition: device: 2695 by Nihon Waters K. K.; column: Capcell Pak C18ACR by Shiseido Co., Ltd. (5 μm, inside diameter 4.6 mm, column length 250 mm); column temperature: 40° C.; mobile phase: tetrahydrofuran/acetonitrile/water/trifluoroacetic acid=350/350/300/2 (v/v/v/v); current speed: 1.0 mL/min.; filling amount: 1 μL; and concentration of a sample: 2000 ppm; (2) MS measurement condition: device: Quatromicro API mass spectrometer by Micromass K. K.; ionization method: ESI (positive mode); capillary voltage: 2.80 KV; flow rate of desolvating gas: 500 L/hour; temperature of desolvating gas: 350° C.; temperature of ion source: 120° C.; and cone voltage: 40 to 60V. Further, the sodium content in the oxidized cyclic phenol sulfide of the present invention was measured by fluorescent X-ray analysis. The measurement was conducted as follows. The oxidized cyclic phenol sulfide was solidified by being pressed to formulate it into a disk shape of 40 to 50 mm in diameter and 3 mm thick. Then, it was measured with a fluorescent X-ray spectrometer (PW2400 produced by Philips).

202.8 g (1.35 mol) of 4-tert-butylphenol, 86.6 g of sulfur (2.71 mol) and 27.0 g (0.675 mol) of sodium hydroxide were poured in a 2 L four-neck flask with a mixer, a cooling tube, a thermometer and a gas-introducing tube. 459 g of diphenyl ether was added thereto and heated up to 130° C. with stirring the mixture in the current of nitrogen gas. The reaction was conducted for 1 hour at 130° C. Then, the temperature was risen to 170° C., and the reaction was conducted for 1 hour at 170° C. Finally, after heating the mixture up to 230° C., the reaction was conducted for 12 hours at 230° C. The above reactions were conducted removing generated water and hydrogen sulfide by the method comprising the steps of letting nitrogen into the reactor and pushing water and hydrogen sulfide out to the system; and contacting them to an aqueous solution of sodium hydroxide to absorb them. The reaction mixture was cooled down to room temperature and neutralized by adding 180 mL of an aqueous solution of 3 mol/L sulfuric acid thereto. Then, 113 mL of toluene and 315 mL of n-hexane were added thereto to precipitate crystals. The crystals were filtered and washed with 360 mL of acetone, 360 mL of water twice, and then 360 mL of acetone to obtain 188.6 g of crystals.

The obtained crystals were analyzed with HPLC. The measurement condition of HPLC is as follows: device: LC-10A by Shimadzu Corporation; column: Develosil ODS-HG-5

(inside diameter 4.6 mm, column length 250 mm) by Nomura Chemical Co., Ltd.; column temperature: 40° C.; mobile phase: tetrahydrofuran/acetonitrile/water/trifluoroacetic acid=450/400/150/2 (v/v/v/v); current speed: 1.0 mL/min.; filling amount: 1 μL; and concentration of a sample: 1000 ppm. As a result of the analysis, it was clarified that the crystals were a cyclic phenol sulfide which comprises a cyclic quatromer wherein R is tert-butyl and m=4 in the formula (1) and a cyclic octamer wherein R is tert-butyl and m=8 in the formula (1); and the relative proportion of a cyclic quatromer to a cyclic octamer is 95:5.

173.1 g (0.24 mol) of the cyclic phenol sulfide wherein the relative proportion of a cyclic quatromer wherein R is tert-butyl and m=4 in the formula (1) to a cyclic octamer wherein R is tert-butyl and m=8 in the formula (1) is 95:5, 692.2 g (fourfold wt/wt) of an acetic acid, 15.8 g (0.048 mol) of sodium tungstate dehydrate and 6.5 g (0.048 mol) of sodium acetate trihydrate were poured in a 2 L four-neck flask with a mixer, a cooling tube and a thermometer, and heated up to 60° C. 373.1 g (3.8 mol) of 35% hydrogen peroxide water was added dropwise thereto for about 2 hours with a drip funnel. After the completion of dropping, the mixture was reacted for 15 hours at 60° C., then for 2 hours at 70° C., and then 3.5 hours at 80° C. 175 g (0.24 mol) of an aqueous solution of 5% (wt/wt) hydrochloric acid was added dropwise thereto at 80° C. and stirred for 1 hour at the same temperature. Then, the mixture was cooled down to room temperature to precipitate a white solid substance. The white solid substance was filtered under reduced pressure, washed with 240 mL of water three times and vacuum dried for 24 hours at 80° C. to obtain 179.2 g (yield 88%) of an oxidized cyclic phenol sulfide.

Figure 2:
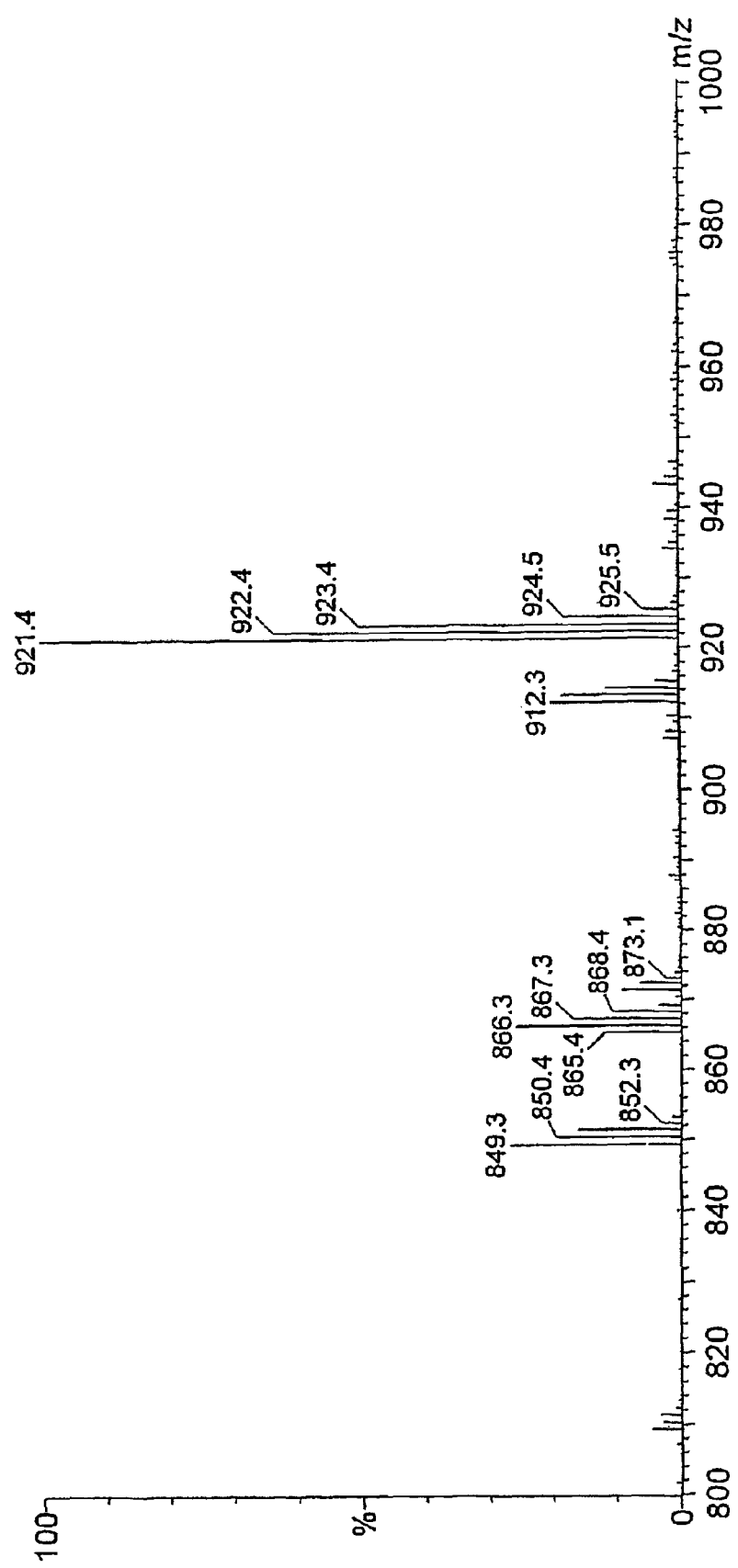
FIG. 2 shows a MS chart of the oxidized cyclic quatromer obtained by Example 1.
Figure 3:
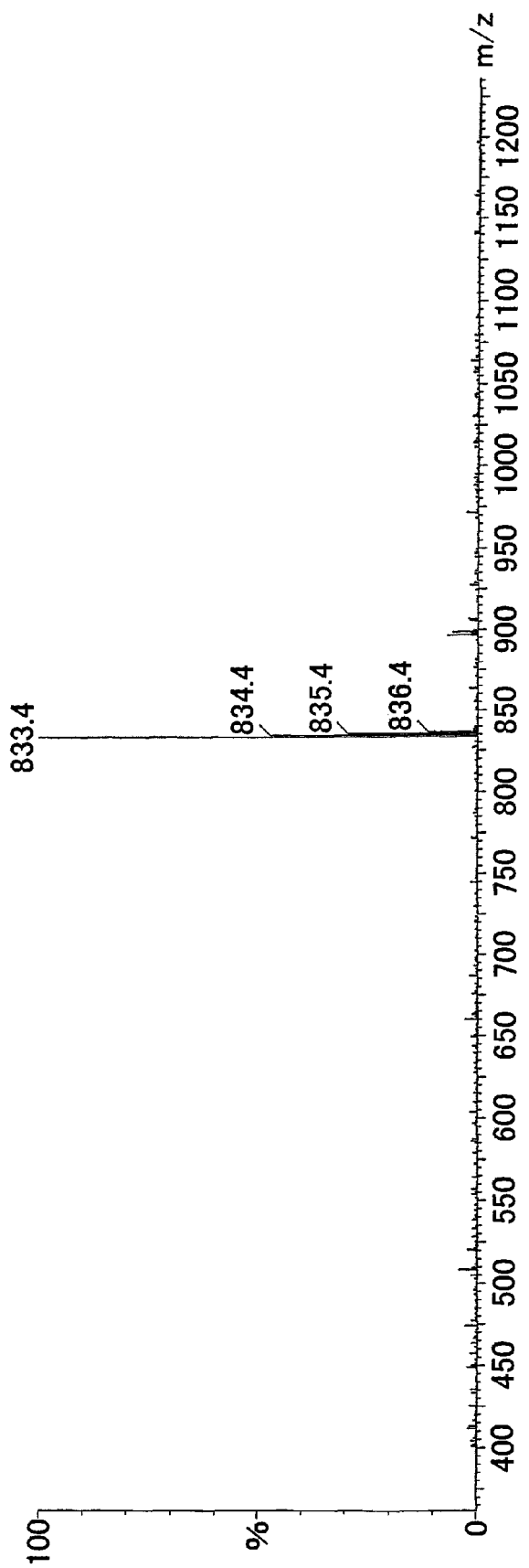
FIG. 3 shows a MS chart of the partially-oxidized form of an oxidized cyclic quatromer obtained by Example 1.
Figure 4:
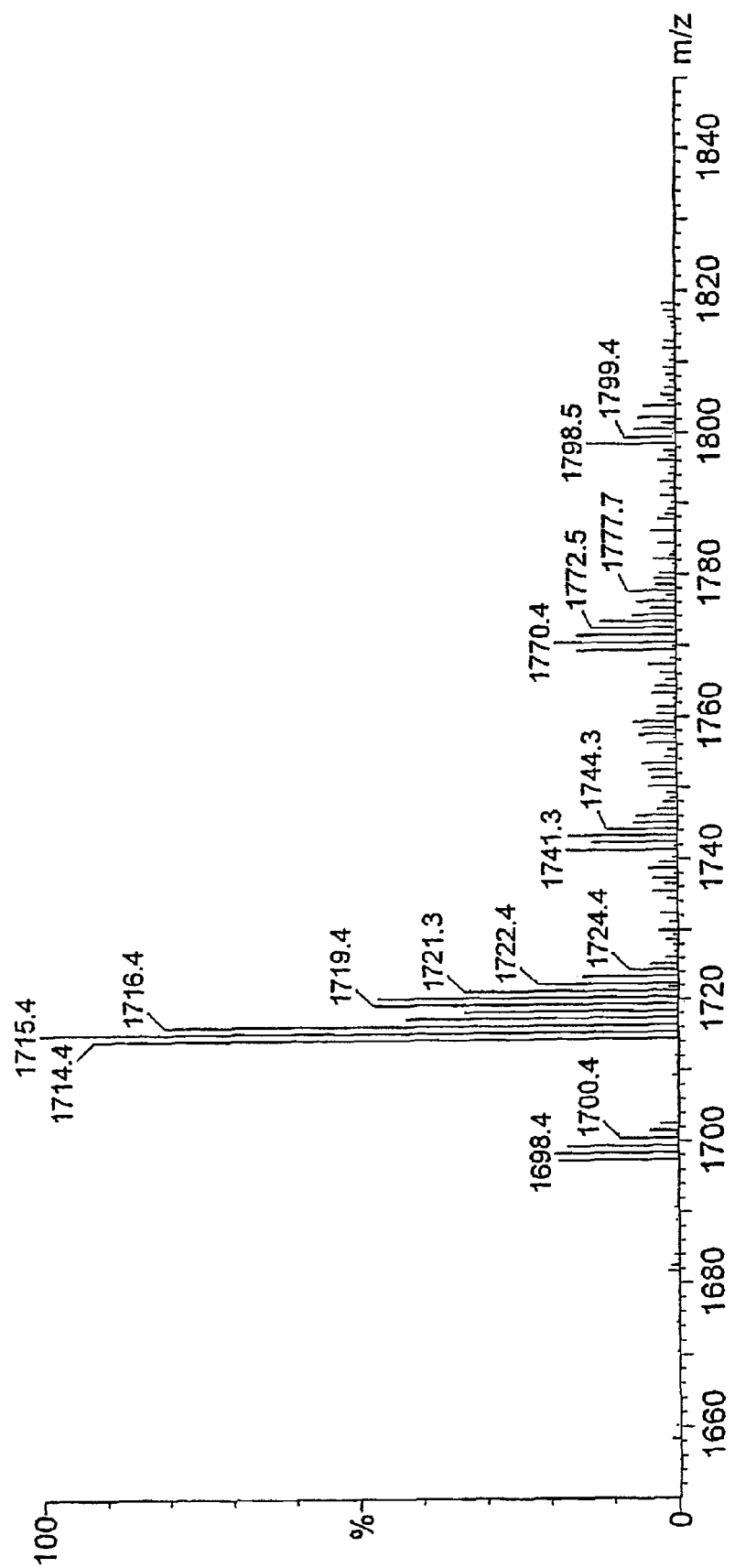
FIG. 4 shows a MS chart of the oxidized cyclic octamer obtained by Example 1.

As a result of LC/MS analysis, the obtained oxidized cyclic phenol sulfide indicated total ion chromatogram (TIC) as indicated in FIG. 1. As a result of the structural analysis, it was confirmed that the oxidized cyclic phenol sulfide comprises an oxidized cyclic quatromer (the oxidized cyclic phenol sulfide wherein R=a tert-butyl group, m=4, and n=2 in the formula (2)); a partially-oxidized form of an oxidized cyclic quatromer {the oxidized cyclic phenol sulfide wherein R=a tert-butyl group, m=4, and there are 7 oxygen on sulfur (n=1 or 2) in the formula (2)}; and an oxidized cyclic octamer (the oxidized cyclic phenol sulfide wherein R=a tert-butyl group, m=8, and n=2 in the formula (2)). The oxidized cyclic quatromer indicated MS spectrum as indicated in FIG. 2. The oxidized cyclic quatromer having molecular weight 848 attributes to m/z=849(M+H), 866(M+NH4), 921(M+H+THF). The partially-oxidized form of an oxidized cyclic quatromer indicated MS spectrum as indicated in FIG. 3. The partially-oxidized form of an oxidized cyclic quatromer having molecular weight 832 attributes to m/z=833(M+H). The oxidized cyclic octamer indicated MS spectrum as indicated in FIG. 4. The oxidized cyclic octamer having molecular weight 1696 attributes to m/z=1697(M+H), 1714(M+NH4), 1769(M+H+THF).

The relative proportions of the obtained oxidized cyclic phenol sulfide by HPLC analysis were as follows: the oxidized cyclic quatromer indicated the peak area ratio of 89.1%; the oxidized cyclic octamer indicated the peak area ratio of 5.7%; and the partially-oxidized form of an oxidized cyclic quatromer indicated the peak area ratio of 1.4%.

Further, the sodium content in the obtained oxidized cyclic phenol sulfide was 551 ppm.

EXAMPLE 2

Since reproducibility is required in the case of applying the present invention industrially, an experiment confirming reproducibility was conducted in the same condition as that of Example 1. As a result, 174.6 g (yield 86%) of an oxidized cyclic phenol sulfide was obtained.

Figure 5:
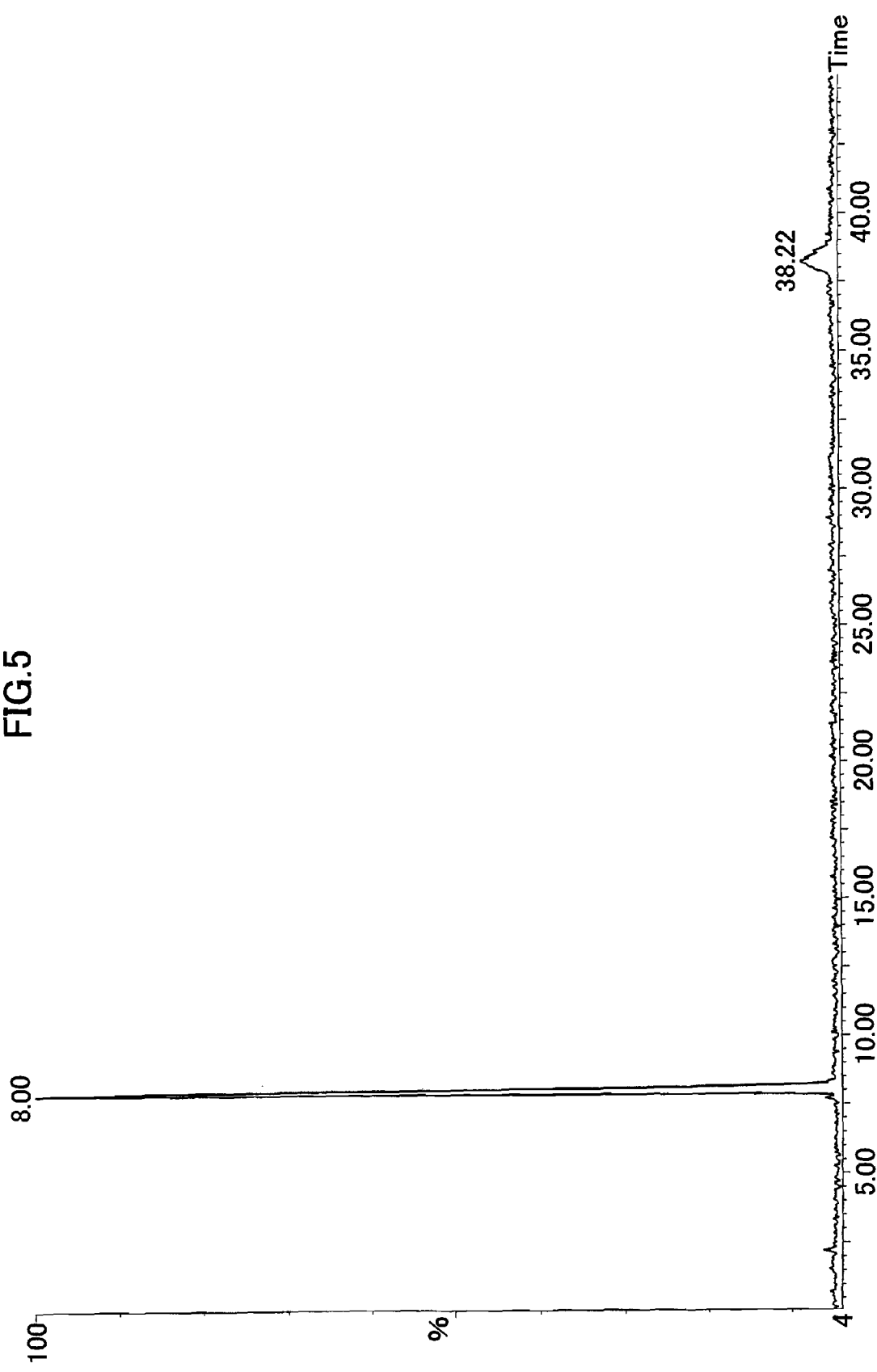
FIG. 5 shows an LC/MS (TIC) chart of the oxidized cyclic phenol sulfide obtained by Example 2.

As a result of LC/MS analysis, the obtained oxidized cyclic phenol sulfide indicated total ion chromatogram (TIC) as indicated in FIG. 5. As a result of the structural analysis, it was confirmed that the oxidized cyclic phenol sulfide comprises an oxidized cyclic quatromer (the oxidized cyclic phenol sulfide wherein R=a tert-butyl group, m=4, and n=2 in the formula (2)) and an oxidized cyclic octamer (the oxidized cyclic phenol sulfide wherein R=a tert-butyl group, m=8, and n=2 in the formula (2)). The relative proportions thereof by HPLC analysis indicated the peak area ratio of the oxidized cyclic quatromer as 90.9%, and the peak area ratio of the oxidized cyclic octamer as 5.8%.

Further, the sodium content in the obtained oxidized cyclic phenol sulfide was 743 ppm.

EXAMPLE 3

A larger-scaled experiment confirming reproducibility was conducted in the same condition as that of Example 1.

1298 g (1.8 mol) of the cyclic phenol sulfide wherein the relative proportion of a cyclic quatromer wherein R is tert-butyl and m=4 in the formula (1) to a cyclic octamer wherein R is tert-butyl and m=8 in the formula (1) is 95:5, 5200 g (fourfold wt/wt) of an acetic acid, 118.7 g (0.36 mol) of sodium tungstate dehydrate and 122.4 g (0.90 mol) of sodium acetate trihydrate were poured in a 10 L four-neck flask with a mixer, a cooling tube and a thermometer, and heated up to 60° C. 2800 g (29 mol) of 35% hydrogen peroxide water was added dropwise thereto for about 3 hours with a drip funnel.

After the completion of dropping, the mixture was reacted for 15 hours at 60° C., then for 2 hours at 70° C., and then 3.5 hours at 80° C. 187.5 g (1.8 mol) of 35% (wt/wt) hydrochloric acid was added dropwise thereto at 80° C. and stirred for 1 hour at the same temperature. Then, the mixture was cooled down to room temperature to precipitate a white solid substance. The white solid substance was filtered under reduced pressure, washed with 1800 mL of water four times and vacuum dried for 24 hours at 80° C. to obtain 1365.5 g (yield 89%) of an oxidized cyclic phenol sulfide.

As a result of LC/MS analysis, the obtained oxidized cyclic phenol sulfide indicated total ion chromatogram (TIC) as indicated in FIG. 6. As a result of the structural analysis, it was confirmed that the oxidized cyclic phenol sulfide comprises an oxidized cyclic quatromer (the oxidized cyclic phenol sulfide wherein R=a tert-butyl group, m=4, and n=2 in the formula (2)) and an oxidized cyclic octamer (the oxidized cyclic phenol sulfide wherein R=a tert-butyl group, m=8, and n=2 in the formula (2)). The relative proportions thereof by HPLC analysis indicated the peak area ratio of the oxidized cyclic quatromer as 92.4%, and the peak area ratio of the oxidized cyclic octamer as 6.2%.

Further, the sodium content in the obtained oxidized cyclic phenol sulfide was 540 ppm.

EXAMPLE 4

An oxidized cyclic phenol sulfide was produced by the same method as that of Example 3, except that 3894 g (threefold wt/wt) of an acetic acid was used. As a result, 1369.5 g (yield 90%) of an oxidized cyclic phenol sulfide was obtained. The relative proportions thereof by HPLC analysis indicated the peak area ratio of the oxidized cyclic quatromer as 90.6%, and the peak area ratio of the oxidized cyclic octamer as 4.8%.

Further, the sodium content in the obtained oxidized cyclic phenol sulfide was 306 ppm.

EXAMPLE 5

An oxidized cyclic phenol sulfide was produced by the same method as that of Example 3, except that 2596 g (double wt/wt) of an acetic acid was used. As a result, 1409.2 g (yield 92%) of an oxidized cyclic phenol sulfide was obtained. The relative proportions thereof by HPLC analysis indicated the peak area ratio of the oxidized cyclic quatromer as 91.8%, and the peak area ratio of the oxidized cyclic octamer as 5.5%.

Further, the sodium content in the obtained oxidized cyclic phenol sulfide was 350 ppm.

COMPARATIVE EXAMPLE 1

When the cyclic phenol sulfide which is the mixture of a cyclic quatromer wherein R is tert-butyl and m=4 in the formula (1) and a cyclic octamer wherein R is tert-butyl and m=8 in the formula (1) is oxidized by the method of the present invention, it is possible to obtain a mixture of an oxidized cyclic quatromer and an oxidized cyclic octamer. However, in the case of conducting the oxidation method of Patent Literature 1, an oxidized cyclic octamer is removed in the solvent extraction step, and only an oxidized cyclic quatromer can be obtained.

2.16 g (3 mmol) of the cyclic phenol sulfide wherein the relative proportion of a cyclic quatromer wherein R is tert-butyl and m=4 in the formula (1) to a cyclic octamer wherein R is tert-butyl and m=8 in the formula (1) is 95:5, 100 mL of chloroform, 65 mL of an acetic acid and 7.39 g (48 mmol) of sodium perborate tetrahydrate were poured in a 300 mL four-neck flask with a mixer, a cooling tube and a thermometer, and heated up to 60° C. After the mixture was reacted for 24 hours at 60° C., 100 mL of hot water was added thereto, and extra sodium perborate was hydrolyzed. Then, an insoluble substance was filtered and washed with 30 mL of chloroform and 100 mL of hot water, respectively, and dried to obtain 0.3 g of a white solid substance. As a result of structural analysis, it was confirmed that the obtained white solid substance mainly comprises an oxidized cyclic octamer (the oxidized cyclic phenol sulfide wherein R=a tert-butyl group, m=8, and n=2 in the formula (2)).

Meanwhile, a filtrate which was obtained after filtering the insoluble substance was separated into a chloroform layer and a water layer, and the water layer was further extracted with 100 mL of chloroform. The obtained extraction solution and said chloroform layer were mixed and washed with 100 mL of hot water. Then, the mixture was dried with anhydrous sodium sulfate, condensed to dryness and vacuum dried to obtain 1.86 g of crystals. The relative proportions of the obtained crystals by HPLC analysis indicated the peak area ratio of the oxidized cyclic quatromer as 93.1%, and the peak area ratio of the oxidized cyclic octamer was undetectable.

COMPARATIVE EXAMPLE 2

86.6 g (0.12 mol) of the cyclic phenol sulfide wherein the relative proportion of a cyclic quatromer wherein R is tert-butyl and m=4 in the formula (1) to a cyclic octamer wherein R is tert-butyl and m=8 in the formula (1) is 95:5 and 3900 g (45 fold wt/wt) of chloroform were poured in a 10L four-neck flask with a mixer, a cooling tube and a thermometer, and heated up to 50° C. to dissolve them. 4550 g (52.5 fold wt/wt) of an acetic acid was added thereto, and then 173.1 g of sodium perborate tetrahydrate crushed in a mortar was further added thereto. The sodium perborate tetrahydrate was gradually dissolved, and almost all thereof was dissolved at 50° C. 1 hour later. The mixture was reacted for 24 hours at 50° C., and a filtrate from which the produced sodium acetate was filtered out was condensed. Then, the precipitated crystals were washed with water and dried to obtain 68.0 g (yield 67%) of white crystals of an oxidized cyclic phenol sulfide. The relative proportions of the obtained crystals by HPLC analysis indicated the peak area ratio of the oxidized cyclic quatromer as 100%, and the peak area ratio of the oxidized cyclic octamer was undetectable.

Further, the sodium content in the obtained oxidized cyclic phenol sulfide was 3780 ppm.

COMPARATIVE EXAMPLE 3

An oxidized cyclic phenol sulfide was produced by the same method as that of Comparative Example 2, except that 2770 g (32 fold wt/wt) of methyl isobutyl ketone was used instead of chloroform. As a result, 68.2 g (yield 67%) of an oxidized cyclic phenol sulfide was obtained. The relative proportions thereof by HPLC analysis indicated the peak area ratio of the oxidized cyclic quatromer as 100%, and the peak area ratio of the oxidized cyclic octamer was undetectable. Further, the sodium content in the obtained oxidized cyclic phenol sulfide was 4210 ppm.

According to the method for producing an oxidized cyclic phenol sulfide of the present invention, since oxidation smoothly proceeds even in the state where the cyclic phenol sulfide of the formula (1), which is the starting material, is dispersed in a solvent(s), there are advantages that solvent usage can be drastically decreased and the reaction time can be shortened. Therefore, it is possible to easily produce the oxidized cyclic phenol sulfide of the formula (2) in high yields, wherein a content of impurities is low, together with improving productive efficiency and decreasing costs as compared to prior arts.

Further, since no halogenated hydrocarbon solvent is used, it is possible to produce the oxidized cyclic phenol sulfide of the formula (2) with reducing environmental burdens.

In addition to them, costs can be decreased and productive efficiency can be improved by using inexpensive hydrogen peroxide. It is also possible to easily filter and separate the reaction mixture without conducting a complicated treatment step to obtain the oxidized cyclic phenol sulfide of the formula (2).

What is claimed is:
1. A method for producing an oxidized cyclic phenol sulfide which comprises the step of oxidizing a cyclic phenol sulfide of the following formula (1) as a raw material:

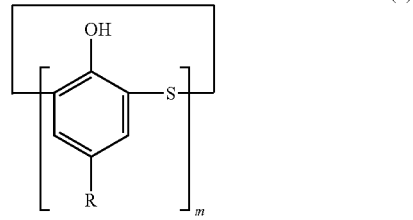

(1)

wherein R represents a straight or branched alkyl group having 1 to 6 carbon atoms, and m is an integer from 4 to 8, in an organic carboxylic acid solvent not comprising a halogen atom in an amount of 2 or more and less than 10 parts by weight per 1 part by weight of the cyclic phenol sulfide, with hydrogen peroxide as an oxidizing agent(s) to obtain an oxidized cyclic phenol sulfide of the following formula (2):

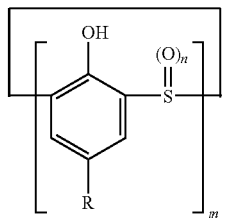

(2)

wherein R represents a straight or branched alkyl group having 1 to 6 carbon atoms, m is an integer from 4 to 8, and n is 1 or 2 wherein no halogenated hydrocarbon is used as a solvent in the oxidation reaction; in the presence of a metal catalyst; wherein the metal catalyst is a tungsten acid or sodium tungstate; and wherein a metal salt of an organic carboxylic acid is used in mole ratios of 0.01 to 5 per 1 mole of the tungsten acid or sodium tungstate; and wherein the metal salt of an organic carboxylic acid is sodium acetate.

2. The method according to claim 1, wherein, in the formula (2), n of each molecules may be the same or different from each other, and each molecule satisfies $1.5\ m \leqq N \leqq 2\ m$ when defining a total of n as N.

3. The method according to claim 1, wherein hydrogen peroxide is used as the oxidizing agent.

4. The method according to claim 3, wherein the cyclic phenol sulfide of the formula (1) is oxidized with hydrogen peroxide in mole ratios of 4 to 24 per 1 mole of said cyclic phenol sulfide in the presence of a solvent(s).

5. The method according to claim 1, wherein the organic carboxylic acid is an acetic acid.

6. The method according to claim 1, wherein 2 to 7 parts by weight of the organic carboxylic acid is used as the solvent per 1 part by weight of the cyclic phenol sulfide of the formula (1).

7. The method according to claim 1, wherein the cyclic phenol sulfide of the formula (1) is oxidized in the presence of 0.01 to 40 mol % of the tungsten acid or sodium tungstate per 1 mole of said cyclic phenol sulfide.

8. The method according to claim 1, which comprises the step of treating the cyclic phenol sulfide of the formula (1) with a mineral acid in mole ratios of 0.01 to 10 per 1 mole of said cyclic phenol sulfide after the completion of the oxidation reaction thereof.

9. The method according to claim 8, wherein the mineral acid is hydrochloric acid or sulfuric acid.

10. The method according to claim 1, wherein the sodium content in the oxidized cyclic phenol sulfide of the formula (2) is 1000 ppm or lower.

11. The method according to claim 1, wherein crystals of the cyclic phenol sulfide of the formula (1) obtained by filtration after the synthetic reaction of the same are used as a raw material of the oxidation reaction without a step of purifying said crystals.

12. The method according to claim 1, wherein, after the addition of the oxidizing agent, the reaction is conducted for 15 to 18 hours at 60° C., then for 2 to 3 hours after being heated up to 70° C., and then for 2 to 5 hours after being heated up to 80° C. or higher.

* * * * *